(12) United States Patent
McKenzie

(10) Patent No.: US 9,237,849 B1
(45) Date of Patent: *Jan. 19, 2016

(54) RELATIVE MAXIMUM INTENSITY PROJECTION

(71) Applicant: Intrinsic Medical Imaging LLC, Bloomfield Hills, MI (US)

(72) Inventor: Lee R. McKenzie, Howell, MI (US)

(73) Assignee: Intrinsic Medical Imaging, LLC, Bloomfield Hills, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/900,640

(22) Filed: May 23, 2013

Related U.S. Application Data

(60) Provisional application No. 61/650,703, filed on May 23, 2012.

(51) Int. Cl.
*A61B 5/00* (2006.01)
(52) U.S. Cl.
CPC .................................... *A61B 5/0033* (2013.01)
(58) Field of Classification Search
CPC ....... G06T 3/0012; G06T 3/4053; G06T 5/50; G06T 7/0026; G06T 2207/20144; G06T 2207/20192; G06T 7/0083; G06T 19/00; G06T 5/20; G06T 17/00; G06T 7/2066; G06T 7/403; G06T 15/08; G06T 2207/30101; G06T 2207/10072; G06T 2207/10081; G06T 19/003; G06T 2200/04; A61B 8/483; A61B 6/466; A61B 8/5207; A61B 2576/00; A61B 8/466
USPC .......................................................... 345/424
See application file for complete search history.

(56) References Cited

U.S. PATENT DOCUMENTS

| 2005/0276455 A1* | 12/2005 | Fidrich et al. ................. 382/128 |
| 2006/0020202 A1* | 1/2006 | Mathew et al. ............... 600/437 |

OTHER PUBLICATIONS

Ruijters, Dynamic Resolution in GPU-Accelerated Volume Rendering to Autostereoscopic Multiview Lenticular Displays, EURASIP Journal on Advances in Signal Processing, vol. 2009, Article ID 843753, 8 pages, pp. 1-8.*

* cited by examiner

*Primary Examiner* — Haixia Du
(74) *Attorney, Agent, or Firm* — David H. Judson

(57) ABSTRACT

A machine-implemented display method that, with respect to a volume dataset being rendered, enables a user to navigate to any position in space and look in any direction. An enhanced display method for this type of dataset improves upon known Maximum Intensity Projection (MIP) techniques. The enhanced method, "Relative MIP," uses a different approach to pixel value rendering. Relative MIP draws information from an amount of difference present between a current pixel and its neighbors, and then visualizes the maximum intensity of this difference.

9 Claims, 10 Drawing Sheets

RELATIVE MAXIMUM INTENSITY PROJECTION

BACKGROUND OF THE INVENTION

1. Technical Field

The technique described herein relates generally to medical imaging.

2. Background of the Related Art

Medical imaging is the technique used to create images of the human body or parts thereof for clinical purposes (medical procedures that seek to reveal, to diagnose or to examine disease) or medical science (including the study of normal anatomy and physiology). Computer tomography (CT) and magnetic resonance imaging (MRI) are two of the most common approaches. These techniques generate a set of individual 2D images that can be displayed in a 3D visualization as a "volume dataset."

In the fields of Radiology and Interventional Cardiology, a particularly important aspect of diagnosing and treating the patient is being able to accurately image the arteries or vessels of the body. Typically, the patient will be given an X-ray CTscan, which creates a collection of consecutive image slices that form a volume of patient data when stacked, or rendered electronically. Several known rendering methods that allow CT data to be viewed have emerged over the years. One of the methods, Maximum Intensity Projection (MIP), fires rays through a volume from a position and a direction, and as it samples each pixel, it looks for the pixel with the greatest intensity along the ray. This maximally intense pixel value is plotted to the screen directly for visualization by a user. A collection of these pixels forms an image where dense structures are able to be seen through less dense structures without regard to the depth of these structures.

MIP-based rendering can be very useful in many circumstances, for example, to see a contrasted artery even when the artery is surrounded by muscle or fat. The problem with a MIP-based approach to viewing an artery, however, is that, while the contrast can easily be seen, the vessel wall is more difficult to discern. It would be very beneficial to be able to determine the diameter of the open area of the artery in relation to the vessel wall when MIP-based rendering is used.

BRIEF SUMMARY

The subject matter disclosed herein, which is sometimes referred to as "Relative MIP," uses a different approach to pixel value rendering that solves the problems associated with the inability to differentiate the vessel wall from the lumen of standard MIP. According to this technique, given a lumen, the open area of the artery, and the pixels in the cross-section of the lumen, the technique assumes that the neighboring pixels, if also part of the lumen, should exhibit a similar value in Hounsfield Units (HU). Conversely, if one of the neighboring pixels is part of the arterial wall, the technique assumes a dissimilar HU value for that pixel. Thus, rather than relying upon an absolute HU value (to discriminate the vessel wall), which value can vary from scan to scan and within the same scan, Relative MIP draws information from the amount of difference present between the current pixel and its neighbors, and then visualizes the maximum intensity of this difference. As a result, an MIP view is created where the actual vessel lumen is distinguished clearly from the vessel wall. A "Maximum Intensity of Relative Hounsfield Units" in MIP mode may then be visualized.

In a preferred embodiment, a final value of a pixel in Relative MIP mode is defined as a maximally intense traversed pixel along a ray, as calculated at each step along the ray, from a sum of the absolute value of the differences between a sampled pixel and its neighboring pixels.

The foregoing has outlined some of the more pertinent features of the disclosed subject matter. These features should be construed to be merely illustrative. Many other beneficial results can be attained by applying the disclosed invention in a different manner or by modifying the invention as will be described.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION

The approach may be implemented in a system such as described below and set forth in the accompanying drawings.

Figure 1:
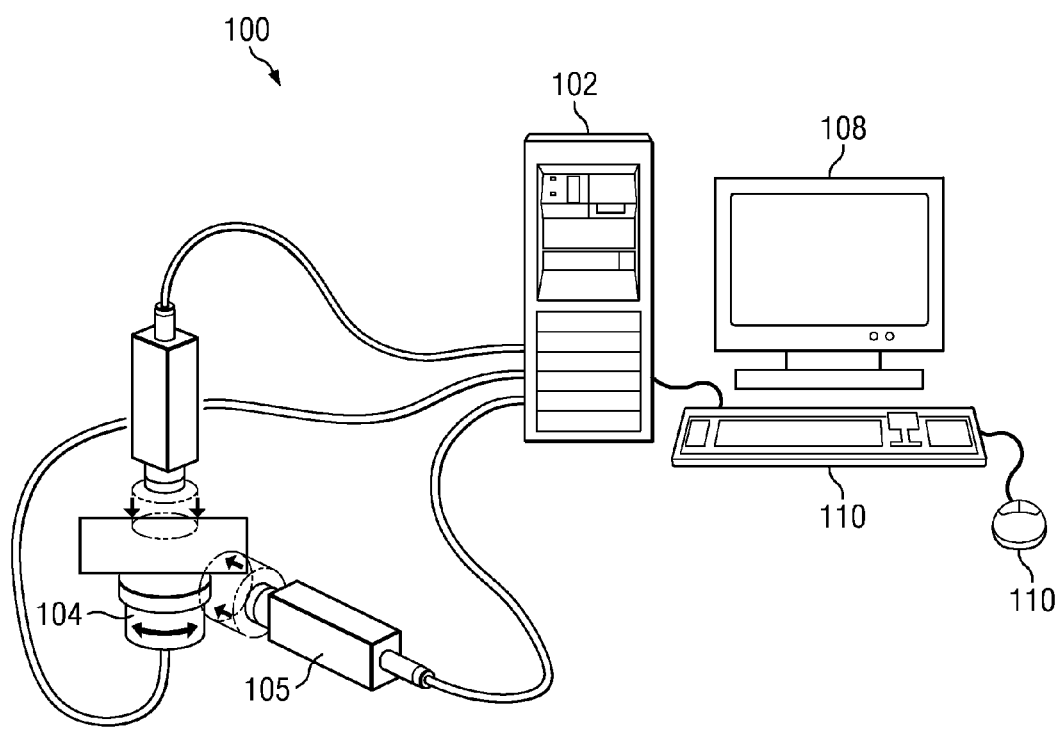
FIG. 1 illustrates a computer system coupled to a medical imaging system.

As illustrated in FIG. 1, a system 100 in which the subject matter herein is implemented comprises a computer system 102 having a display monitor 108, and one or more input devices 110 such as a keyboard, a pointing device, or the like. The computer system 102 is illustrated as a desktop workstation, but this is not a limitation, as the system may be implemented in a laptop or notebook computer, a wireless computing device (such as an iPad), or any other computing machine that includes a display. The techniques of this disclosure are not limited to any particular type of computing device, system or architecture, and one or more of the elements of the machine may be located in different locations. Thus, for example, the display monitor may be positioned remotely from other components. For convenience of illustration only, the computer system 102 is shown as receiving inputs from a pair of imaging devices 105 that are associated with a support 104. The support 104 rotates or reciprocates relative to the imaging devices 105 to generate a set of individual 2D images of an object being scanned. Typically, the support 104 has associated mechanical elements, hydraulic elements and/or electronic elements (not shown) that control the position or rotational speed thereof. The support may be under computer control. Likewise, the one or more imaging devices 105 include associated optical elements, mechanical elements, and/or other control elements that control the position and operation of the device. Typically, an object to be imaged (e.g., a human body, or some part thereof) is located on the support 104. The support may be fixed, in which case the imaging devices 105 rotate or reciprocate with respect thereto. One of ordinary skill in the art will appreciate that the support 104 and imaging devices 105 represent conventional medical imaging systems such as computer tomography (CT), magnetic resonance imaging (MRI), or the like. Typically, such systems are external to the imaging system of this disclosure, although the imaging techniques herein may be implemented natively within such known imaging systems. The 2D images comprising a particular scan typically conform to a standard digital data format (e.g., DICOM) and are received by the computer system 102 in any convenient manner, e.g., a CD, DVD, USB stick, hard drive, network drive, PACS (a medical CT library), or the like. Of course, the computer system 102 may be network-accessible, in which case the digital data comprising the volume data may be received over a communication network, such as any Internet Protocol (IP)-based network, a wireline network, a wireless network, or the like.

As noted above, this disclosure provides a display method, preferably implemented in a computer, such as a workstation as shown in FIG. 1. More generally, the method is implemented using one or more computing-related entities (systems, machines, processes, programs, libraries, functions, code, or the like) that facilitate or provide the inventive functionality. In a representative but non-limiting implementation, the display methods described herein are implemented in a machine comprising a CPU (central processing unit), such as any Intel- or AMD-based chip, computer memory, such as RAM (at least 1 GB), a hard drive (at least 8 GB), and a CD-drive (preferably 24-48×). The machine software includes an operating system (e.g., Windows XP, Windows Vista, Windows 7, any Apple OS, either 32 bit or 64 bit), and generic support applications. If the process is implemented in a graphics processor, preferably the machine comprises a graphics processing unit (GPU) such as the AMD Radeon Series 4850 or equivalent (preferably at least DirectX 9-compliant and Pixel Shader 3.0-compliant).

Figure 2:
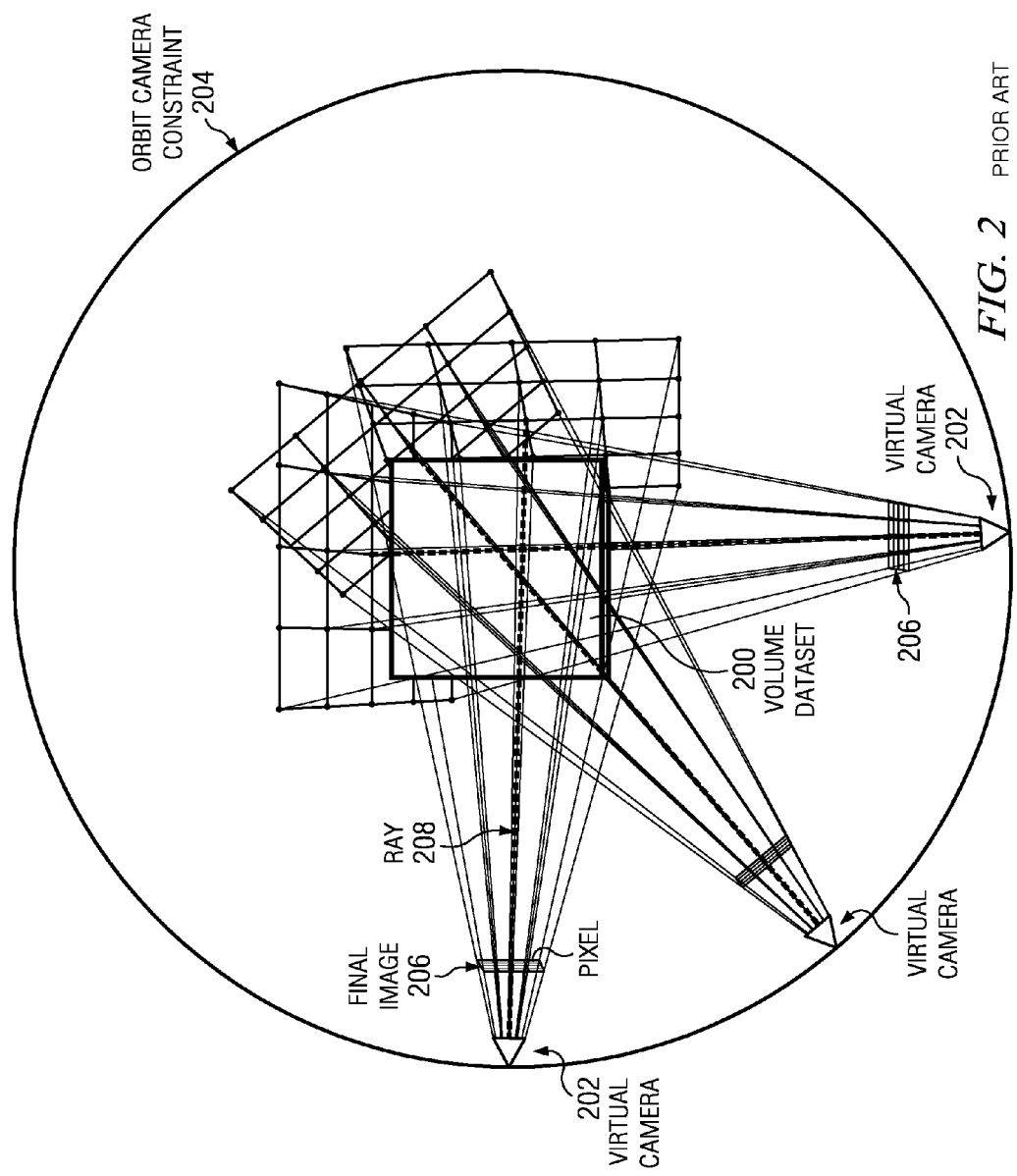
FIG. 2 illustrates a technique for rendering and "orbiting" about a volume dataset.
Figure 3:
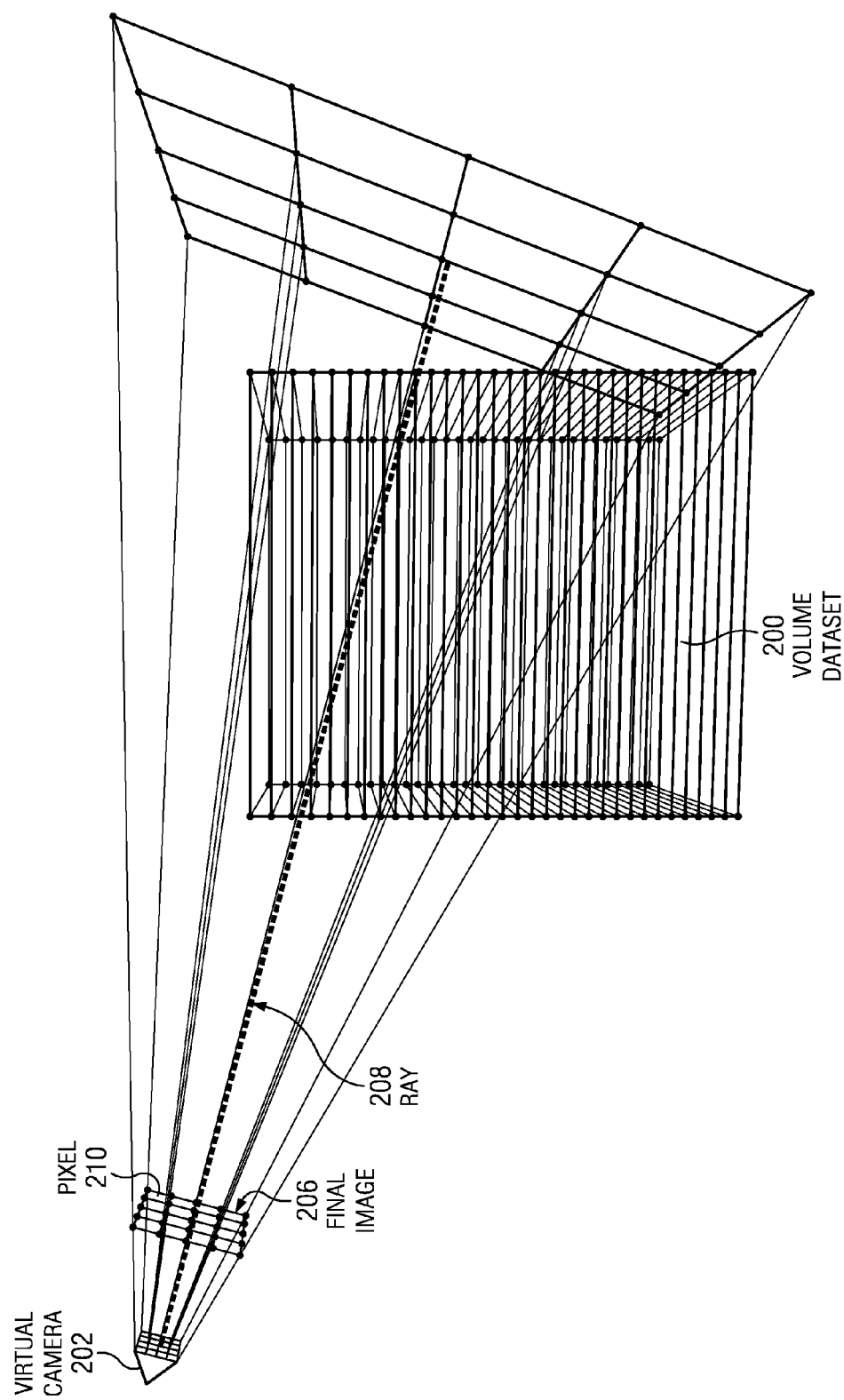
FIG. 3 illustrates how ray tracing is used to generate a final image using a virtual camera.

By way of background, FIG. 2 illustrates a known technique for visualizing a volume dataset 200. The volume dataset is a stack or assembly of 2D images forming a cube (or 3D dataset). In this approach, a virtual camera 202 orbits around the dataset along the constraint 204, which constraint is shown in the drawing as a circle but is actually a sphere in three dimensions. The virtual camera 202 is a machine-implemented software-generated construct that has a position, an orientation, and a resolution. The virtual camera renders a final image 206 at a display rate by ray tracing. In the drawing, a single virtual camera is shown at various positions along the orbital constraint. In each position, the virtual camera produces a final image in the manner illustrated in FIG. 3. Ray tracing is a process by which a set of rays are cast forward into the volume dataset from the virtual camera and intersected with structures therein to produce the final image comprising a set of pixels. In particular, a ray 208, which is a line with a direction located at a point in space, is cast forward into the scene to find an intersection point or multiple intersection points that contribute to the final value (brightness or color) for a single pixel 210 in the final image. Each "ray" is generated in software and simulates light generated from the camera. The virtual camera is "operated" (once again, virtually) at a given frame rate (or frames "per second"). Thus, if the frame rate is 24, the virtual camera produces the final image 206 every second with 24 distinct frames in an image sequence. Each frame comprising a number of 2D pixels. The pixels in a particular frame are uniform in that they are of the same size. Any individual pixel in the volume dataset is sometimes referred to as a voxel.

Figure 4:
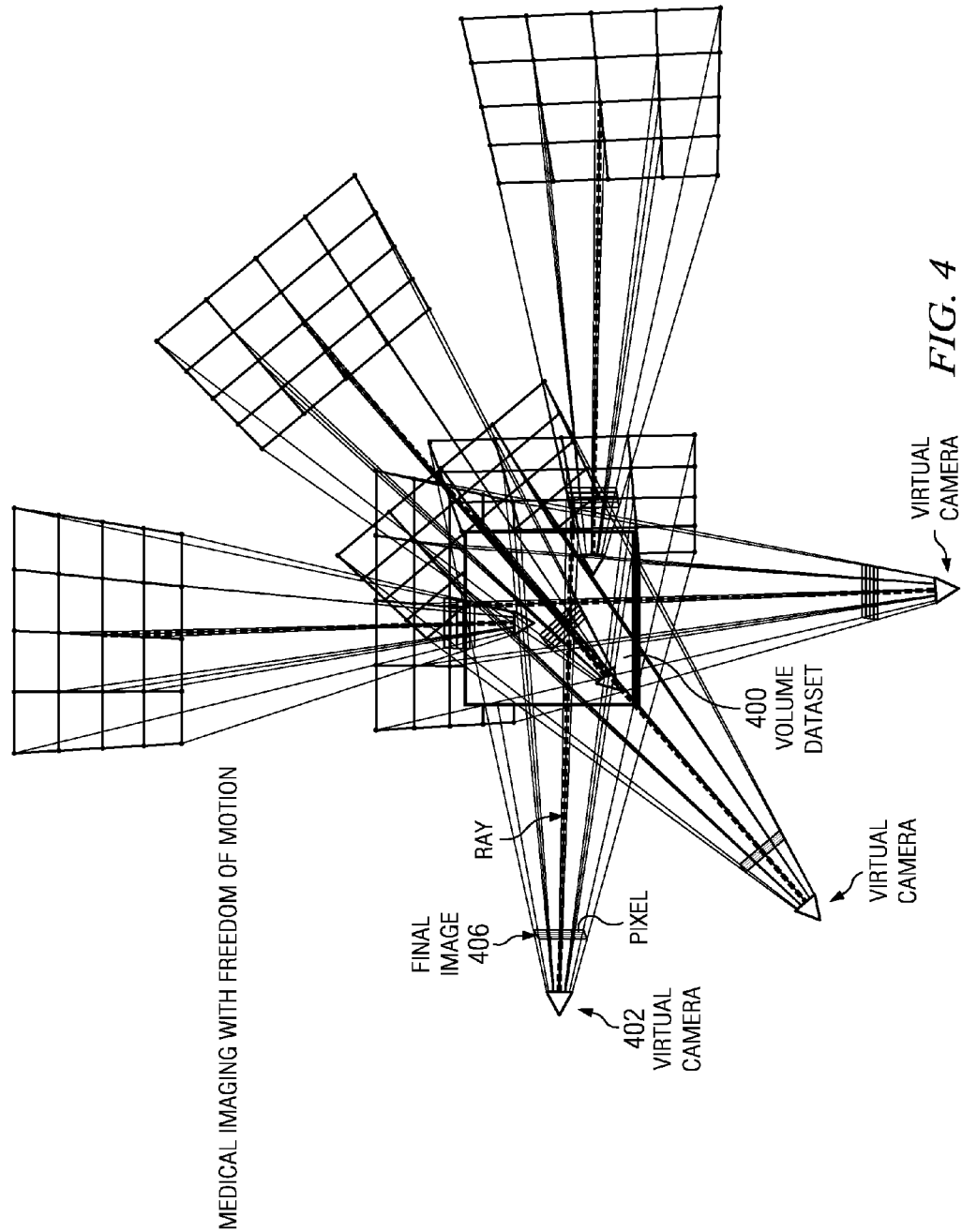
FIG. 4 illustrates the technique of this disclosure for rendering and viewing a volume dataset from any position external to or within the dataset.

Although it provides some basic interactivity, the "orbit" approach illustrated in FIG. 2 is quite limiting. FIG. 4 illustrates the approach of the subject disclosure, wherein the volume dataset 400 is rendered using a virtual camera 402 that displays the final image 406 without any position constraint. In this approach, the virtual camera 402 may be moved to any position outside or even within the volume dataset. Several of these internal positions are illustrated. In this novel approach, the virtual camera is movable (using the input device) inside the volume dataset, and the viewer can navigate along and through internal structures that are represented therein. Thus, according to this approach, and unlike the prior art, the viewer has full freedom-of-motion within and around the volume dataset, or any portion thereof. This degree of interactivity provides a significantly enhanced and valuable user experience, as it provides much greater detail of internal structures. The technique allows the user to explore the human body non-invasively from every position and direction possible. The virtual camera (and thus the viewer) can move past tissue that might otherwise block a view, and the camera can present views from inside the body that were previously unattainable. In effect, the technique enables the viewer to see through multiple types of tissue simultaneously and to examine the spatial relationship of different parts of the body.

There are two (2) techniques that facilitate the disclosed method: (i) continuous real-time dynamic rendering resolution, and (ii) continuous per pixel dynamic sampling distance for ray tracing volume datasets. Each of these techniques is now described.

As used herein, "resolution" refers to a spatial number of pixels horizontally and vertically, with respect to a picture (image) that is drawn from a particular display frame. "Rendering" refers to a process by which the eventual picture is drawn by the disclosed technique. In a representative embodiment, rendering is implemented by ray tracing, although this is not a limitation. The term "dynamic" refers to changes to the output rendering resolution at each frame, or as needed. The term "real-time" generally refers to a frame per second update rate greater than a predetermined value, such as 24. The term "continuous" refers to the number of pixels that are added to or subtracted from a final picture every frame to ensure that the picture only changes a small amount, to ensure smoothness. The "continuous real-time dynamic rendering resolution" function changes a number of pixels horizontally and vertically by a small amount in relation to a difference between a current frame rate and a desired frame rate, with respect to a picture that is drawn at a frame update rate (preferably >24 frames per second) to provide high resolution rendering. This feature is beneficial as it allows higher rendering quality than is possible for fixed resolution, which cannot guarantee real-time frame rates especially with respect to any position in space.

Figure 5:
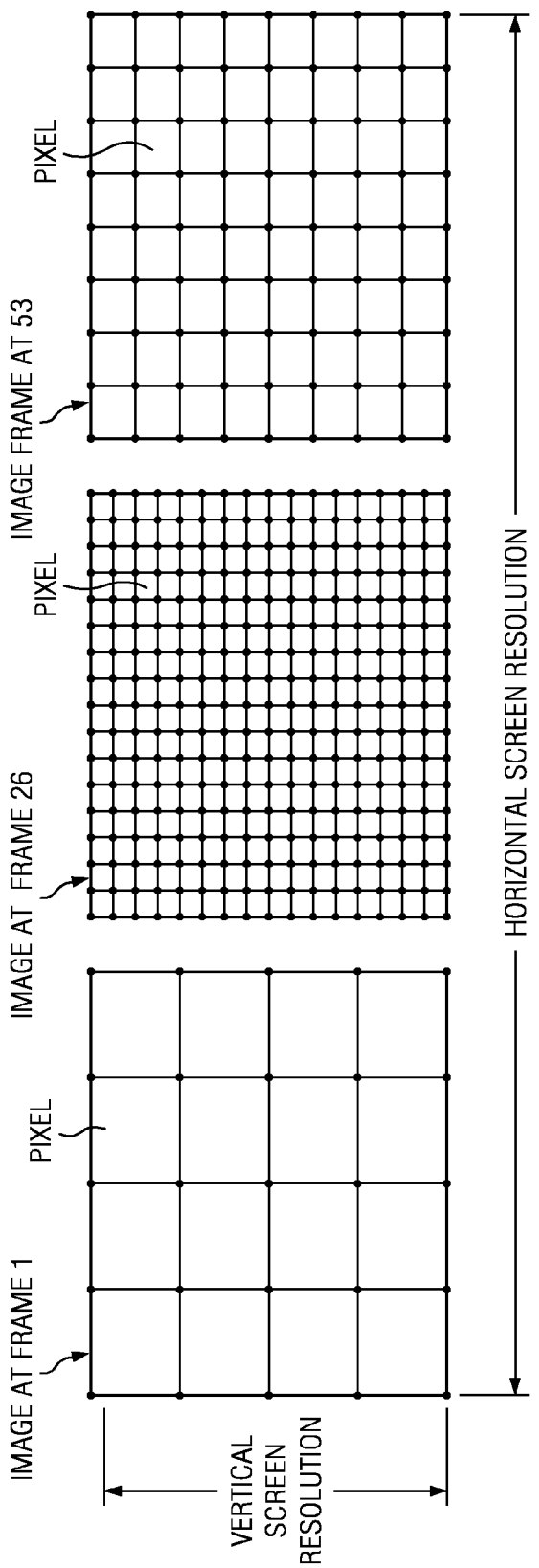
FIG. 5 illustrates a dynamic rendering resolution technique of this disclosure.

The dynamic rendering resolution is illustrated in FIG. 5. This figure shows three (3) representative (random) frames of a set of display frames of the displayed image. Each frame represents a single final image, and the set of final images (from the set of frames) represent the displayed image as rendered on the display at a given point in time. As illustrated, each pixel in each frame is uniform, although according to the "dynamic rendering resolution" function of this disclosure, the resolution can vary across particular frames. Thus, in this example, frame 1 as 16 pixels, frame 26 has 256 pixels, and frame 53 has 64 pixels. Generalizing, when an image of the volume dataset is rendered at a given number of frames per second, at least two frames in the image sequence have varying resolution.

This dynamic rendering resolution function preferably is achieved as follows. Inside a main display processing loop, and at a minimum of "desired" frames per second, the routine calculates a difference between a "current" frame rate and a "desired" frame rate. This frame rate difference is what determines how the resolution will change for this frame. When the difference is positive (i.e., when the desired frame rate is greater than current frame rate), the display routine use one less pixel column or pixel row alternately (or one less of each) in the final image to render a next frame. This operation "speeds up" the rendering application and helps achieve the desired frame rate. If, on the other hand, the difference in frame rate is negative (i.e., the desired frame rate is less than the current frame rate), the display routine uses one more pixel column or pixel row alternately (or one more of each) in the final image to render the next frame. This increases the rendering resolution and, thus, the quality of the rendered image. At the end of each frame, the routine rescales the image back to screen resolution with or without interpolation to account for the change in the number of pixels. This process speeds up the rendering because ray tracing is inherently very dependent on the total number of cast rays in the final image. If that number is reduced, the application speeds up.

Figure 6:
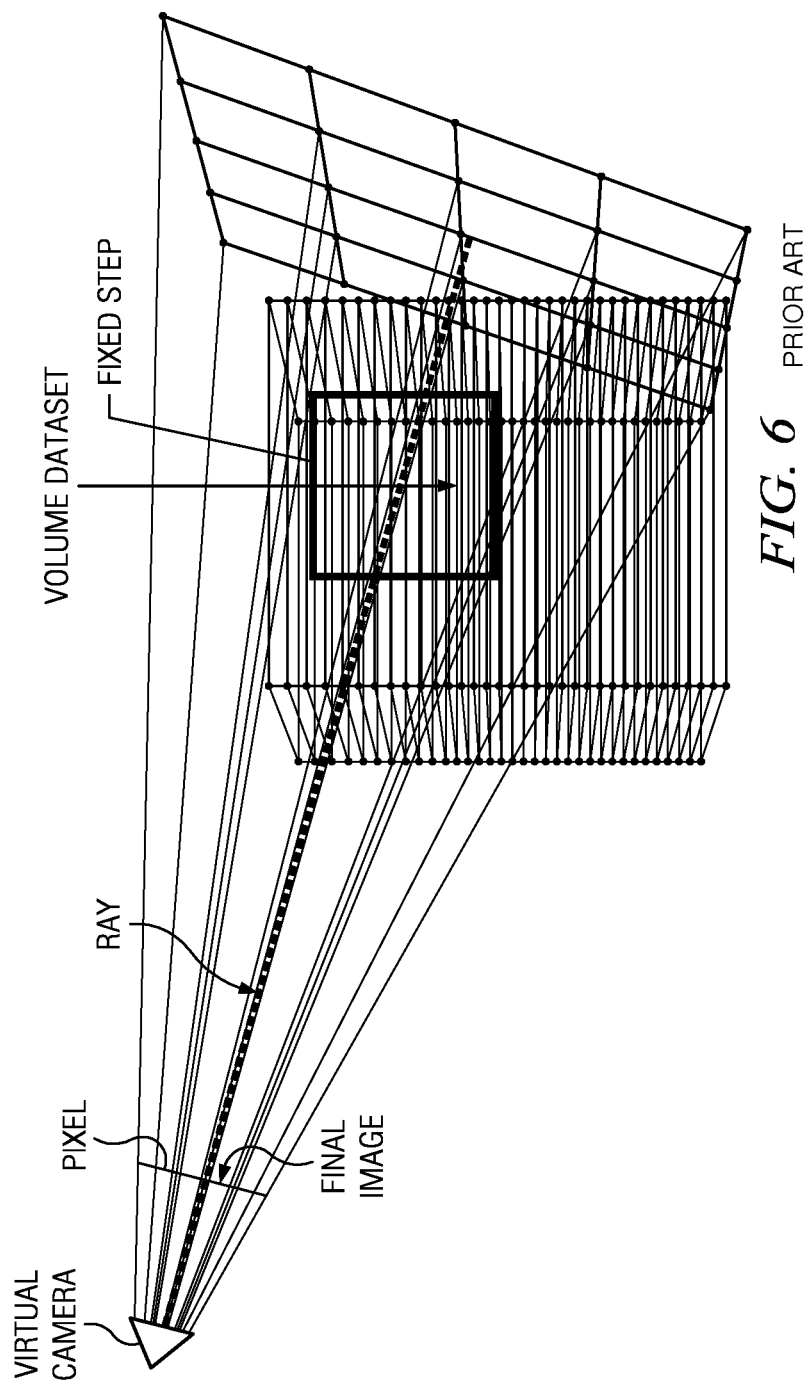
FIG. 6 illustrates a fixed step ray tracing technique.
Figure 7:
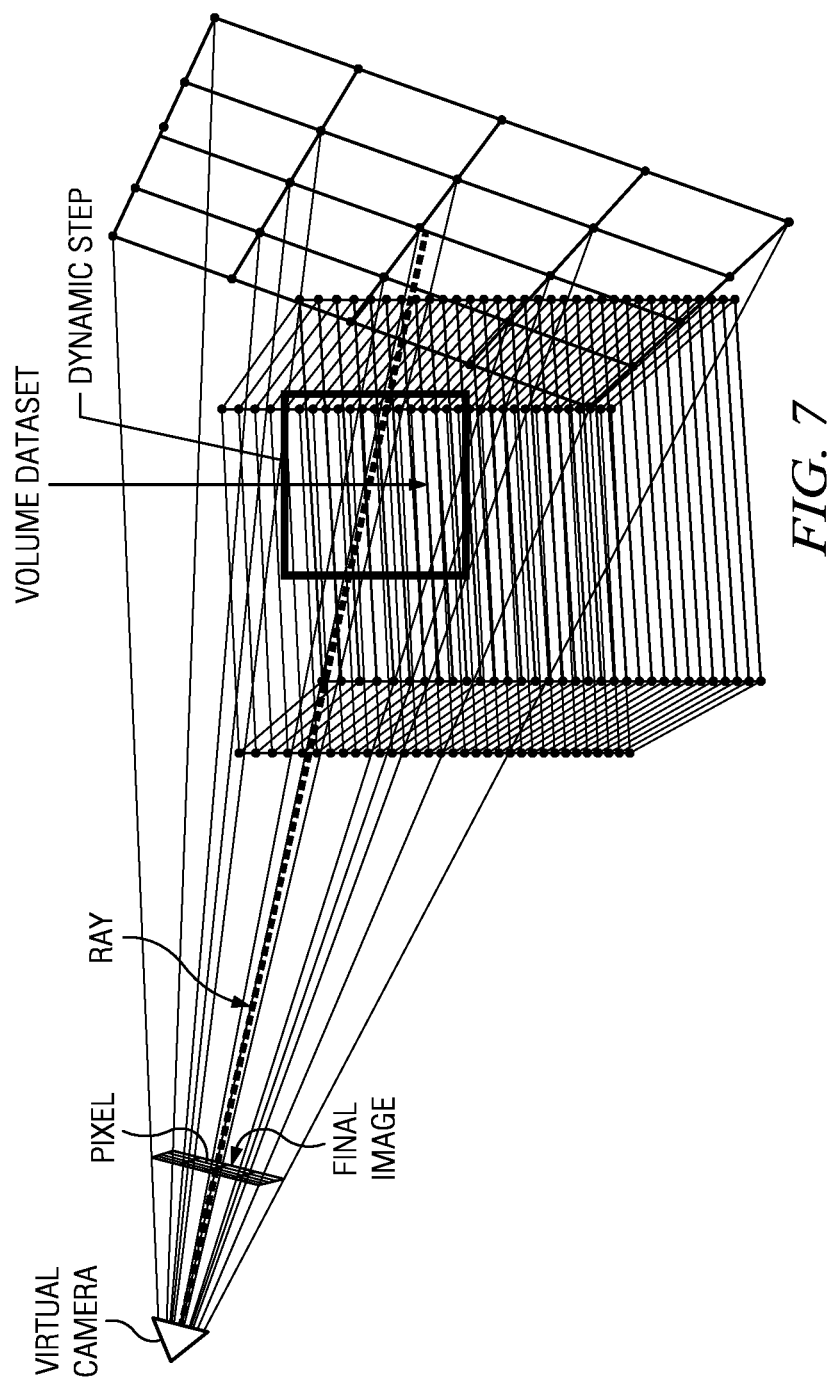
FIG. 7 illustrates a dynamic step ray tracing technique of this disclosure.

In addition to dynamic rendering resolution, the display method of this disclosure implements an approach referred to as "continuous per pixel dynamic sampling distance for ray tracing," as is now described. By way of background, FIG. 6 illustrates a "fixed step" approach wherein the distance from each previous sampling location (represented by a dot) along the length of the ray is the same. This fixed step pattern does not take into consideration the characteristics of the volume dataset itself (e.g., the density at the particular intersection point in the CT scan, or the value of electron spin at the particular point in the MRI scan), but simply generates the sample at a particular uniform location along the ray. This fixed step approach does not produce satisfactory results. According to this disclosure, the sampling distance along the length of a ray is permitted to vary dynamically within each pixel. Preferably, the step changes after a sampling of the dataset (and, in particular, after each sampling) and in relation to a value contained in the dataset. Further, preferably a distance added to or subtracted from a current step along the ray preferably is small to ensure smoothness as the ray traverses through the dataset. In a preferred embodiment, each ray (each corresponding to a pixel) adjusts its own unique step dynamically as it traverses through and samples the dataset. In effect, the ray speeds up or slows down as needed. For every pixel in the output image on a per sample basis, the display routine adjusts the unique sampling distance along the length of the ray cast forward in space, which represents a single pixel in the rendered image, in relation to the values sampled from the dataset. Generalizing, at least first and second pixels within a particular frame have a varying number of ray tracing steps relative to one another. This approach facilitates high-resolution rendering at real-time frame rates while avoiding any restrictions on the virtual camera in terms of its position and orientation in space.

A preferred approach to implementing the per-pixel dynamic sampling distance for ray tracing is now described. For every frame at real time rates, and for every pixel in the final image, the routine "starts" the ray at the camera position. Then, the routine sets the ray's direction to be the camera direction plus the pixel position in the image transformed into world space. This operation amounts to an aperture or lens for the 3D camera; as a result, the ray has both a position and a direction. The program then steps down the ray, stopping at locations to sample the volume dataset. The distance that is stepped each frame is dependent on the value at the current sample point of the volume data and a value (e.g., CT density, MRI electron spin, or equivalent) of the desired tissue in current focus. Preferably, and as described above, the distance stepped equals an absolute value of the difference between the currently sampled value (e.g., density) and the user- or system-configured target, multiplied by a small number to ensure smoothness. In general, if the absolute value of the difference in desired tissue value and current sampled volume data is high, then a larger step is taken. If, however, the value of the difference in desired tissue value and current sampled volume data is small, then a smaller step is taken.

Figure 8:
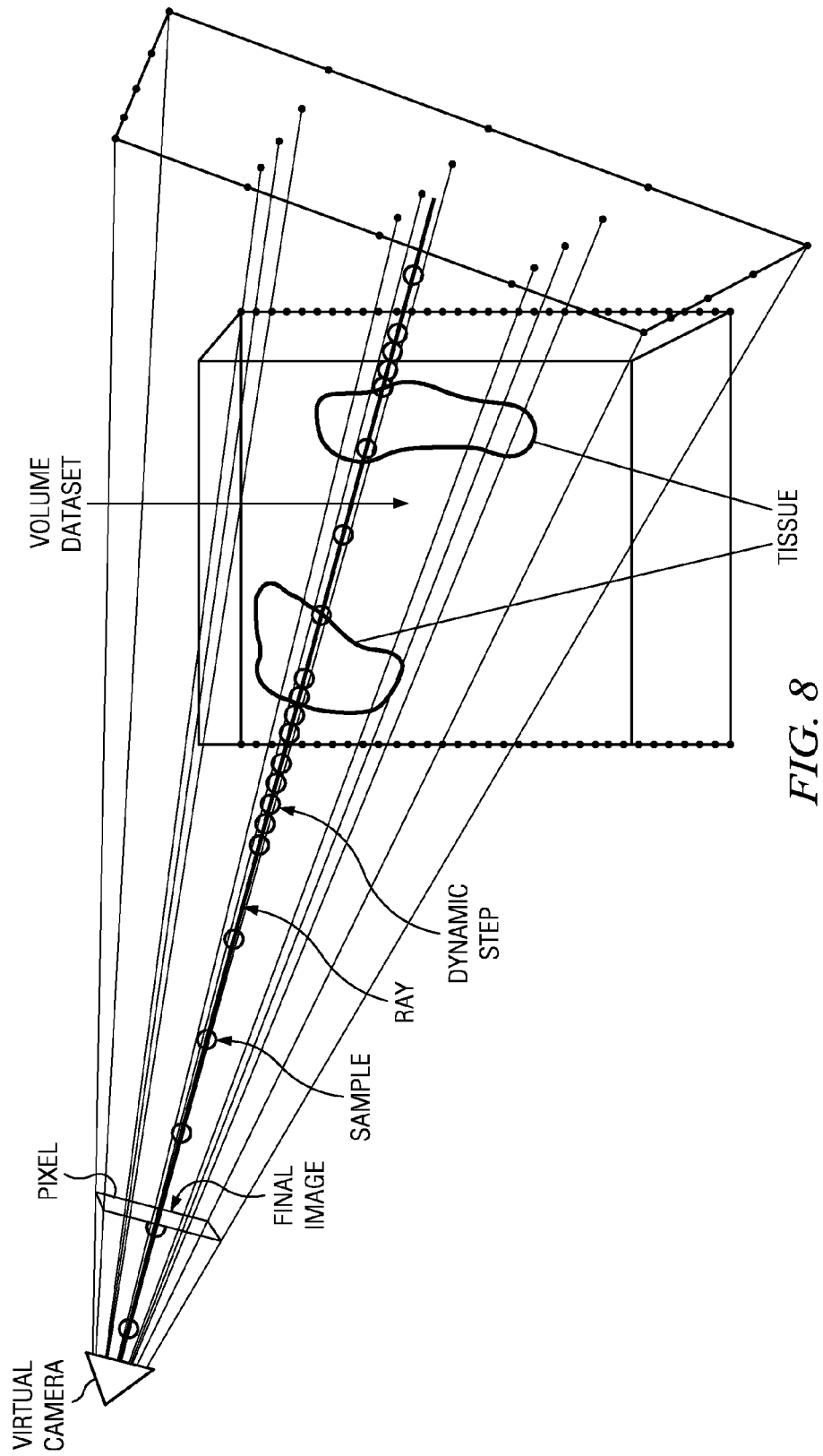
FIG. 8 illustrates the dynamic stepping approach showing how the number of steps varies along the ray in areas where tissues are located.
Figure 9:
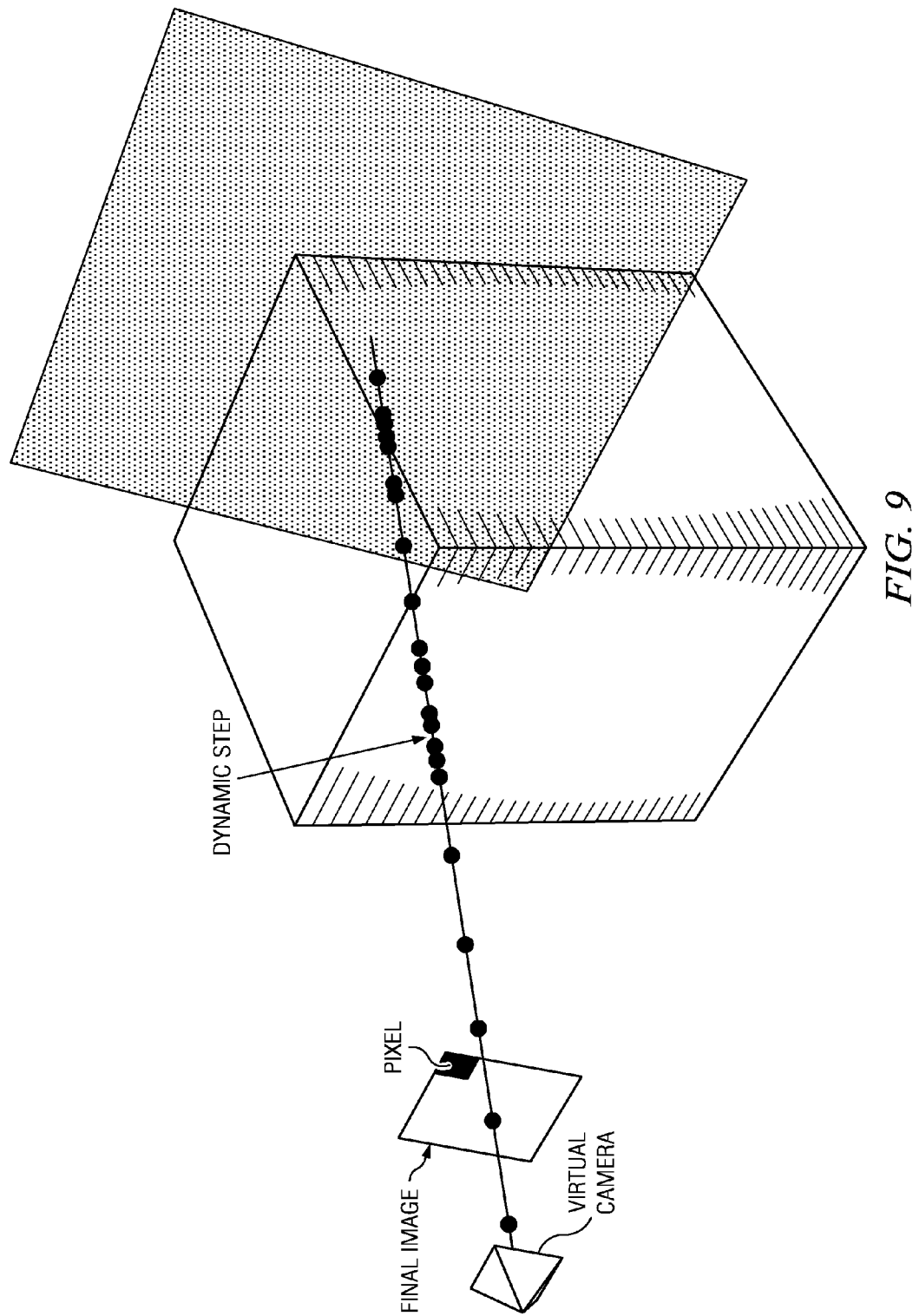
FIG. 9 is another view showing the dynamic stepping approach of FIG. 8.

Preferably, and as illustrated in FIGS. 8-9, the process concentrates the steps and samples in areas where the desired tissue values exist, while areas that are not in focus are spared (i.e., need not be subjected to dynamic stepping). At each step, preferably the routine takes the scalar sampled volume data value and scales it (e.g., to the range of −1000 to 1000 standard Hounsfield units), and then the routine uses this value to look-up a color that corresponds to a certain type of material based on the Hounsfield number. (In the alternative, the value can be used directly for grey-scale images.) The routine then uses an accumulation method (e.g., pixel color equals tissue difference multiplied by the step color) to accumulate the color for this step onto the pixel itself. Preferably, at each step, a small value is added to the accumulated density. This process is repeated either until density is greater than a desired value or until the step distance itself is very small (e.g., a desired small value beyond which the eye can see), or until the maximum known depth is reached. When finished, the routine has the final color for this pixel. Preferably, this approach is then repeated for every pixel in the final image.

When it is time for the next frame to be rendered, the camera is moved to its new position and orientation, and then process is repeated again.

For computational efficiency, the above-described approach may be implemented using a GPU so that many pixels can be processed in parallel. In the alternative, a multi-core CPU can be used to facilitate the parallel processing.

Figure 10:
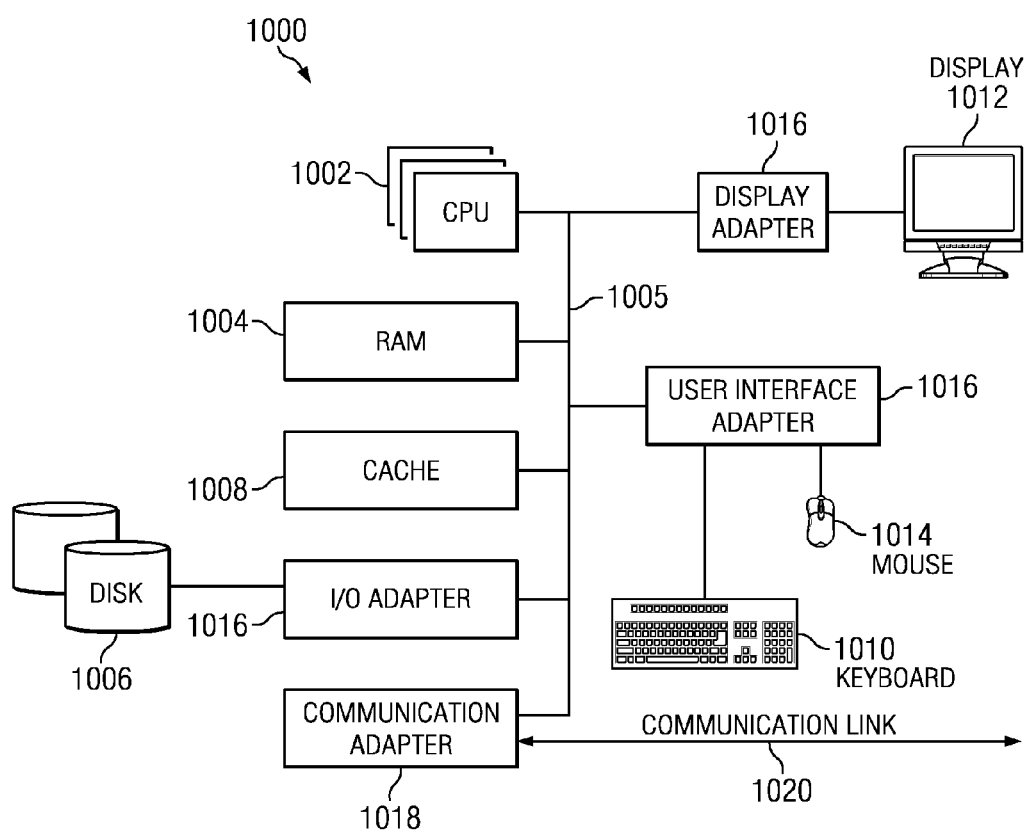
FIG. 10 is a machine in which the disclosed visualization methods may be implemented.

FIG. 10 illustrates a representative data processing system 1000 for use in processing the digital data. A data processing system 1000 suitable for storing and/or executing program code will include at least one processor 1002 coupled directly or indirectly to memory elements through a system bus 1005. The memory elements can include local memory 1004 employed during actual execution of the program code, bulk storage 1006, and cache memories 1008 that provide temporary storage of at least some program code to reduce the number of times code must be retrieved from bulk storage during execution. Input/output or I/O devices (including but not limited to keyboard 1010, display 1012, pointing device 1014, etc.) can be coupled to the system either directly or through intervening I/O controllers 1016. Network adapters 1018 may also be coupled to the system to enable the data processing system to become coupled to other data processing systems or devices through networks 1020. The rendering program that implements dynamic rendering resolution and dynamic per-pixel ray tracing is stored in system local memory 1004, as are the data structures and associated data generated during the rendering process. As noted above, in an alternative embodiment, the data processing system includes a GPU and associated graphics card components and, in this case, preferably the rendering program and volume data are stored in graphics card memory.

Maximum Intensity Projection

A maximum intensity projection (MIP) is a known volume rendering method for 3D data that projects in a visualization plane the voxels with maximum intensity that fall in the way of parallel rays traced from a viewpoint to the projection plane. Further information about the technique can be found in the publication titled "Three-dimensional display in nuclear medicine," by Wallis et al, *IEEE Trans Med Imaging* 8 (4): 297-303.

Relative Maximum Intensity Projection

With the above as background, the following describes the subject matter of this disclosure.

As described above, the subject matter disclosed herein, which is sometimes referred to as "Relative MIP," uses a different approach to pixel value rendering that solves the problems associated with the inability to differentiate the vessel wall from the lumen of standard MIP. According to this technique, given a lumen, the open area of the artery, and the pixels in the cross-section of the lumen, the technique assumes that the neighboring pixels, if also part of the lumen, should exhibit a similar value in Hounsfield Units (HU). Conversely, if one of the neighboring pixels is part of the arterial wall, the technique assumes a dissimilar HU value for that pixel. Thus, rather than relying upon an absolute HU value (to discriminate the vessel wall), which value can vary from scan to scan and within the same scan, Relative MIP draws information from the amount of difference present between the current pixel and its neighbors, and then visualizes the maximum intensity of this difference. As a result, an MIP view is created where the actual vessel lumen is distinguished clearly from the vessel wall. A "Maximum Intensity of Relative Hounsfield Units" in MIP mode may then be visualized.

Visually, when comparing a traditional MIP view of an artery to the Relative MIP view, there is a noticeable difference. The traditional MIP view shows an artery as a solid, soft gradient vessel. Meanwhile, Relative MIP depicts an artery as an open vessel with a surrounding wall. Further, when a plaque exists in the wall of the artery, it can also be natively visualized from the relative MIP, since its HU value is vastly different from the surrounding tissue. When viewing plaques from a Relative MIP view, the inner lining of the arterial wall that surrounds the plaque is actually visible. This is in contrast to traditional MIP in which the arterial wall itself is not easily distinguishable from the contrasted lumen.

In a preferred embodiment, a final value of a pixel in Relative MIP mode is defined as a maximally intense traversed pixel along a ray, as calculated at each step along the ray, from a sum of the absolute value of the differences between a sampled pixel and its neighboring pixels.

While certain aspects or features have been described in the context of a computer-based method or process, this is not a limitation of the invention. Moreover, such computer-based methods may be implemented in an apparatus or system for performing the described operations, or as an adjunct to other dental restoration equipment, devices or systems. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including optical disks, CD-ROMs, and magnetic-optical disks, read-only memories (ROMs), random access memories (RAMs), magnetic or optical cards, or any type of media suitable for storing electronic instructions, and each coupled to a computer system bus. The described functionality may also be implemented in firmware, in an ASIC, or in any other known or developed processor-controlled device.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

While given components of the system have been described separately, one of ordinary skill will appreciate that some of the functions may be combined or shared in given systems, machines, devices, processes, instructions, program sequences, code portions, and the like.

The volume dataset may be generated from any data source. It is not required that the volume dataset be CT or MRI data, or that the data itself be medical imaging data. The techniques herein may be used within any volume dataset irrespective of content.

A tangible, non-transitory machine-readable medium stores the computer program that performs the dynamic rendering resolution and dynamic per-pixel ray tracing during the process of rendering the volume dataset on the display. The program receives the volume dataset and renders the virtual camera construct (which lives inside the machine). The program moves and re-orients the camera under the user's control, altering the view as desired. As described, the dynamic rendering resolution process increases or decreases the number of pixels in each frame of a set of frames, while the per-pixel dynamic stepping increases or reduces the number of ray tracing steps per pixel. By continuously reducing the resolution across frames and reducing the number of steps per pixel within a frame, the program can speed up its overall rendering of the image at the desired frame rate, and in this manner the virtual camera construct can be positioned and oriented anywhere, including within the volume dataset itself. The virtual camera has complete freedom-of-motion within and about the volume dataset; thus, the viewer has the ability to move to any position in 3D space and look in any direction in real-time. The described approach enables real-time tissue selection and segmentation in 3D so that various tissues (including bone) are visualized without requiring the program to continually re-build a 3D mesh or to use preset tissue palettes.

The invention claimed is:

1. An article comprising a tangible, non-transitory machine-readable medium that stores a program, the program being executed by a machine having a hardware component to perform a method, the method comprising:

receiving a volume dataset defining a volume within a human body; and rendering, with respect to any position and orientation in the volume, an image sequence of the volume dataset at a given number of frames per second, each frame of the image sequence having pixels that are uniform, at least two frames of the image sequence having varying resolution, the image sequence representing a lumen, an open area of an artery, and pixels in a cross-section of the lumen;

wherein a given pixel in a frame has a value that is defined as a maximally intense traversed pixel along a ray, as calculated at each step along the ray, from a sum of an absolute value of differences between a sampled pixel and its neighboring pixels in the cross-section of the lumen;

wherein neighboring pixels that are part of the lumen and within the cross-section are rendered with a first value, and neighboring pixels that are part of a wall of the artery are rendered in a second value dissimilar to the first value such that the wall of the artery is visually distinguishable from the lumen.

2. The article as described in claim 1 wherein the amount of difference is measured in Hounsfield Units.

3. The article as described in claim 2 further including providing a visualization of a maximum intensity of relative Hounsfield Units.

4. Apparatus, comprising:
a display;
a processor; and
computer memory holding computer program instructions that, when executed by or in association with the processor, render a 3D image on the display at a frame rate with two frames of an image sequence having varying resolution with respect to one another, the 3D image representing a lumen, an open area of an artery, and pixels in a cross-section of the lumen, wherein a given pixel in a frame has a value that is defined as a maximally intense traversed pixel along a ray, as calculated at each step along the ray, from a sum of an absolute value of differences between a sampled pixel and its neighboring pixels in the cross-section of the lumen;

wherein neighboring pixels that are part of the lumen and within the cross-section are rendered with a first value, and neighboring pixels that are part of a wall of the artery are rendered in a second value dissimilar to the first value such that the wall of the artery is visually distinguishable from the lumen.

5. The apparatus as described in claim 4 wherein the amount of difference is measured in Hounsfield Units.

6. The apparatus as described in claim 4 wherein the display provides a visualization of a maximum intensity of relative Hounsfield Units.

7. A display method, comprising:
receiving a volume dataset defining a volume within a human body; and rendering, using a hardware processor, and with respect to any position and orientation in the volume, an image sequence of the volume dataset from a perspective of a virtual camera, at least two frames of the image sequence having varying resolution with respect to one another, the image representing a lumen, an open area of an artery, and pixels in a cross-section of the lumen;

wherein a given pixel in a frame has a value that is defined as a maximally intense traversed pixel along a ray, as calculated at each step along the ray, from a sum of an absolute value of differences between a sampled pixel and its neighboring pixels in the cross-section of the lumen;

wherein neighboring pixels that are part of the lumen and within the cross-section are rendered with a first value, and neighboring pixels that are part of a wall of the artery are rendered in a second value dissimilar to the first value such that the wall of the artery is visually distinguishable from the lumen.

8. The method as described in claim 7 wherein the amount of difference is measured in Hounsfield Units.

9. The method as described in claim 7 further including providing a visualization of a maximum intensity of relative Hounsfield Units.

* * * * *